United States Patent [19]
Feltz et al.

[11] Patent Number: 4,871,546
[45] Date of Patent: Oct. 3, 1989

[54] GASTROINTESTINAL PROTECTIVE COATING FORMULATIONS

[75] Inventors: Dennis R. Feltz, Succasunna; Saul S. Kornblum, Springfield; Samuel B. Stoopak, West Caldwell, all of N.J.

[73] Assignee: Sandoz Pharm. Corp., E. Hanover, N.J.

[21] Appl. No.: 184,656

[22] Filed: Apr. 22, 1988

Related U.S. Application Data

[63] Continuation of Ser. No. 67,989, Jun. 29, 1987, abandoned, which is a continuation of Ser. No. 534,830, Sep. 22, 1983, abandoned.

[51] Int. Cl.$^4$ ................................................. A61K 9/32
[52] U.S. Cl. ................................................... 424/482
[58] Field of Search ......................................... 424/482

[56] References Cited

U.S. PATENT DOCUMENTS

| | | | |
|---|---|---|---|
| 2,702,264 | 2/1955 | Klaui | 424/482 |
| 3,096,248 | 7/1963 | Rudzki | 424/472 |
| 3,325,365 | 6/1967 | Hotko et al. | 424/482 |
| 4,060,598 | 11/1977 | Groppenbacher et al. | 424/482 |

FOREIGN PATENT DOCUMENTS 907309 10/1962 United Kingdom ............... 424/482

*Primary Examiner*—Shep K. Rose
*Attorney, Agent, or Firm*—Gerald D. Sharkin; Robert S. Honor; Walter F. Jewell

[57] ABSTRACT

Tablet formulations for the diffusable release of drugs in the gastrointestinal tract, which formulations protect the gastric mucosa from the effects of solid, gastric irritating drugs. The formulation comprises a drug tablet core, coated with a water permeable, gastrointestinal fluid insoluble polymeric coating, e.g., polymethyl methacrylate, polyethylene glycol polyvinylacetate, diethylphthalate and dioctyl sodium sulfosuccinate.

2 Claims, No Drawings

GASTROINTESTINAL PROTECTIVE COATING FORMULATIONS

This is a continuation of application Ser. No. 067,989, filed June 29, 1987 now abandoned which in turn is a continuation of application Ser. No. 534,830, filed Sept. 22, 1983, now abandoned.

This invention relates to polymeric film formulations. More particularly this invention relates to polymeric film formulations which provide tablet coatings with diffusible release characteristics that protect the gastric mucosa from the effects of solid, gastric irritating drugs.

When gastric irritating drugs such as potassium chloride are used, the tablet coating protects the gastric mucosa from irritation by drug particles. Prior art enteric coating are available which prevent particulate drug release in the gastric region. However, these coatings do not allow for a diffused release of a drug in the gastrointestinal area.

Diffusable release of a drug from a coated tablet formulation entails the permeation of the film coating by the gastrointestinal fluid and the hydration of the dosage form. During hydration the film coating swells—to about twice its size—and forms a sack about the disintegrating tablet core. The drug leaves the sack in solution form and thus is non-irritating to the gastric mucosa. To accomplish this a diffusable coating must be water permeable and gastrointestinal fluid insoluble.

Diffusable release of a drug regulates the quantity of drug released from a drug formulation at a particular time and/or particular site. Diffusable release has the advantage of providing medication over a period of time without the sudden release of large amounts of particulate drug.

This invention provides polymeric water permeable and gastrointestinal fluid insoluble film formulations. When applied to gastric irritating drug table cores, the polymeric film both protects the gastric mucosa from the drug, and provides for a diffused release of the drug in the gastrointestinal area.

The diffused release polymeric film coatings of this invention may comprise:

| Polymer Coating | Amount - Parts by Weight |
|---|---|
| Polymethyl Methacrylate[1] | 10 to 30 |
| Polyethylene Glycol[2] | 20 to 55 |
| Polyvinylacetate[3] | 20 to 60 |
| Diethyl Phthalate | 5 to 10 |
| Dioctyl Sodium Sulfosuccinate | 0.2 to 1.0 |

Preferably the polymeric film coating may comprise:

| Polymer Coating | Amount - Parts by Weight |
|---|---|
| Polymethyl Methacrylate | 15 to 25 |
| Polyethylene Glycol | 25 to 50 |
| Polyvinylacetate | 25 to 55 |
| Diethyl Phthalate | 6 to 8 |
| Dioctyl Sodium Sulfosuccinate | 0.4 to 0.6 |

[1]Polymethyl Methacrylate 100,000 to 500,000, average molecular weight
[2]Polyethylene Glycol 1,000 to 6,000, average molecular weight
[3]Polyvinylacetate 12,000 to 167,000, average viscosity molecular weight A preferred diffusable release polymeric film coating of this invention may comprise:

| Polymer Coating | Amount - Parts by Weight |
|---|---|
| Polymethyl Methacrylate | 10 to 30 |
| Polyethylene Glycol | 20 to 55 |
| Polyvinylacetate | 20 to 60 |
| Diethyl Phthalate | 5 to 10 |

Preferably the polymeric film coating may comprise:

| Polymer Coating | Amount - Parts by Weight |
|---|---|
| Polymethyl Methacrylate | 15 to 25 |
| Polyethylene Glycol | 25 to 50 |
| Polyvinylacetate | 25 to 55 |
| Diethyl Phthalate | 6 to 8 |

The polymeric film coated diffused release drug tablets of this invention may be prepared by first preparing the drug tablet core and then coating the core.

The tablet core may be prepared in a conventional manner by screening the ingredients through a conventional stainless steel screen, e.g., #20 mesh, blending the resultant powders in a conventional blending apparatus, granulating the blend, and then compressing the granulation into tablets.

The tablets may be coated by preparing a solution of the polymeric film coating, applying the coating to the tablets in a conventional automatic air spray coating apparatus at a temperature of from ambient to 60° C., preferably ambient to 40° C., the drying the polymer coated tablets.

Various types of drugs may be used in the tablet core such as antihistamines, hypoglycemics, antidepressants. cardiovascular agents, psychotherapeutic agents, e.g., thioridazine, ergot alkaloids, antibiotics and the like.

The tablet core may also contain conventional tableting ingredients, e.g., lubricants, talc and the like.

EXAMPLE 1

Polymeric coated tablets were prepared having the following composition:

| Tablet Core Ingredients | Amount Per Tablet |
|---|---|
| Potassium Chloride, U.S.P. | 600 mg |
| Starch 1500[1] | 65 mg |
| Stearic Acid, U.S.P. | 20 mg |
| Polyvinylpyrrolidone[2] | 15 mg |
| Tablet Core Weight | 700 mg |

[1]Pregelatinized Starch, NF, Colorcon, Inc., West Point, Pa. 12–20% cold water solubility
[2]Povidone U.S.P., GAF Corp., New York, New York

| Polymer Coating Ingredients | Amount Per Tablet | | |
|---|---|---|---|
| Polymethyl Methacrylate[3] | 2.00 mg | 3.00 mg | 4.00 mg |
| Polyethylene Glycol 4000 | 4.30 mg | 6.45 mg | 8.60 mg |
| Polyvinylacetate[4] | 2.95 mg | 4.425 mg | 5.90 mg |
| Dioctyl Sodium Sulfosuccinate[5] | 0.05 mg | 0.075 mg | 0.10 mg |
| Diethyl Phthalate | 0.70 mg | 1.050 mg | 1.40 mg |
| Coating Weight | 10.00 mg | 15.00 mg | 20.00 mg |

-continued

| Polymer Coating Ingredients | Amount Per Tablet | | |
|---|---|---|---|
| Coated Tablet Weight | 710.0 mg | 715.0 mg | 720.0 mg |

[3]Plexiglas VS, Rohm and Haas, Spring House, PA
[4]AYAF Resin, Union Carbide Corp., New York, NY 113,000 average viscosity molecular weight
[5]Aerosol OT (solid), American Cyanamid A batch of 85,000 (59.5 kg) polymer coated potassium chloride tablets were prepared as follows:

51 kg of potassium chloride, 5.525 kg of Starch 1500 and 1.7 kg of stearic acid was screened through a #20 mesh stainless steel screen. The powders were then blended in a planetary mixer for 20 minutes. The blended powders were then granulated with a solution of 1.275 kg of polyvinylpyrrolidone in 4 kg of purified water. [Additional purified water may be added to obtain the proper granule wetness (about 0.5 to 1 kg is usually sufficient)]. The granulation was then dried, sized and compressed into 700 mg tablets.

Tablet Specifications

Tablet Weight: 700 mg
Tablet Thickness: 5.5–5.6 mm
Tablet Shape: 11 mm, round, deep convexity
Tablet Hardness: 6–9 Strong-Cobb Units A 10 kg batch of the potassium chloride tablets were coated with the polymer coating.

EXAMPLE 2

The coated tablets prepared in Example 1 were tested for dissolution rate analysis. The dissolution rate of potassium ion from the tablets was determined as follows:

The potassium ion was determined using a potassium-specific ion electrode (Orion model 92-19) with a reference electrode (Single-Junction Orion model 90-01 with a 4M lithium trichloroacetate filing solution, Orion #90-00-19) and a mV meter.

A standard solution equivalent to 100% of the theoretical amount was prepared fresh using potassium chloride that has been dried overnight. Dilutions were prepared to given concentrations equivalent to 10%, 20% and 50% of the theoretical amount. All four solutions were placed in a 37° C. water bath. After equilibration, the mVs of each solution were measured and the values obtained were plotted against the equivalent concentrations (mole/liter) on a 2 cycle semi-log graph paper.

The concentration (mole/liter), equivalent to a 100% release, was calculated as follows:

$$M = \frac{\text{Dosage (g)} \times 10^3}{74.55} \times \frac{1}{100} *$$

74.55 is the molecular weight of potassium chloride and 1/500 is the dilution factor.
*For a 600 mg dosage, $M = 1.61 \times 10^{-2}$ The straight line obtained by joining the four points is the calibration curve used to calculate the percent potassium ion released at each time interval.

The procedure and apparatus used for continuous-flow dissolution rate of the potassium chloride tablets of Example 1 is that basically disclosed by C. Cakiryildiz et al., Dissolution Studies with a Multichannel Continuous-flow Apparatus, J. Pharm. Sci., Vol. 64, No. 10, October 1975, p. 1692-1696.

The continuous-flow apparatus consisted of:

(a) five identical independent dissolution cells immersed in a constant temperature bath maintained at 37°±0.5° C.

(b) one reservoir vessel is connected to each dissolution cell. The reservoirs contained 500 ml of distilled water as the medium, stirred at high speed and immersed in a constant temperature bath of 37°±0.5° C.

(c) the two electrodes (described above) are placed in the water medium.

(d) a five channel peristaltic pump had one channel connected to each dissolution cell and its reservoir vessel.

The results of the continuous-flow dissolution rate tests of the potassium chloride tablets of Example 1 is shown in the following table I, II and III wherein each test is an average of three tablets.

The polymer coating on each tablet remained intact throughout each test. The results show that the polymeric tablet coating of this invention gave a satisfactory release rate of potassium ion over the four hour test period, without a release of solid potassium chloride from the tablet.

TABLE I

| Time | 10 mg Coating % Potassium Chloride Released | | | |
|---|---|---|---|---|
| Hours | 1 | 2 | 3 | Mean |
| 1 | 71.4 | 62.1 | 64.0 | 65.8 |
| 2 | 92.5 | 97.5 | 97.5 | 95.8 |
| 2.5 | 100.0 | 105.6 | 100.0 | 103.3 |
| 3 | — | 109.9 | 105.6 | 105.2 |
| total % released | 100.0 | 109.9 | 105.6 | 105.2 |

TABLE II

| Time | 15 mg Coating % Potassium Chloride Released | | | |
|---|---|---|---|---|
| Hours | 1 | 2 | 3 | Mean |
| 1 | 57.8 | 43.5 | 55.9 | 52.4 |
| 2 | 80.7 | 79.5 | 88.2 | 81.1 |
| 3 | 93.2 | 95.1 | 102.6 | 94.6 |
| 3.5 | 100.0 | — | 109.9 | — |
| 4 | — | 100.0 | — | 103.3 |
| total % released | 100.0 | 100.0 | 109.9 | 103.3 |

TABLE III

| Time | 20 mg Coating % Potassium Chloride Released | | | | | |
|---|---|---|---|---|---|---|
| Hours | 1 | 2 | 3 | 4 | 5 | Mean |
| 1 | 27.9 | 48.4 | 37.3 | 37.3 | 34.2 | 37.0 |
| 2 | 48.4 | 79.5 | 67.1 | 67.1 | 64.0 | 64.2 |
| 3 | 60.2 | 88.2 | 93.2 | 93.2 | 93.2 | 85.6 |
| 3.5 | 71.4 | — | 97.5 | 97.5 | 97.5 | 90.4 |
| 4 | 80.7 | — | — | — | 100.0 | 92.9 |
| 4.5 | 88.2 | — | — | — | — | 94.3 |
| total % released | 88.2 | 88.2 | 97.5 | 97.5 | 100.0 | 94.3 |

EXAMPLE 3

Polymeric coated tablets were prepared having the tablet core of Example 1 and coated with:

| Polymer Coating Ingredients | Amount per Tablet |
|---|---|
| Polymethyl Methacrylate[3] | 2.0 mg. |
| Polyethylene Glycol 4000 | 4.3 mg. |

| Polymer Coating Ingredients | Amount per Tablet |
|---|---|
| Polyvinylacetate[4] | 3.0 mg. |
| Diethyl Phthalate | 0.7 mg. |
| Coating Weight | 10.0 mg. |
| Coated Tablet Weight | 710.0 mg. |

[3]Plexiglas VS, Rohm and Haas, Spring House, PA
[4]AYAF Resin, Union Carbide Corp., New York, NY 113,000 average viscosity molecular weight.

A 10 kg. batch of the potassium chloride tablets were coated with the polymer coating.

The polymer solution used for coating was prepared by adding with constant stirring 43.8 g. of polymethyl methacrylate, 94.2 g. of polyethylene glycol 400, 65.7 g. of polyvinylacetate, and 15.3 g. of diethyl phthalate, to a solution of 0.777 kg. of methanol, absolute and 2.004 kg. of methylene chloride.

The 10 kg. tablet batch was coated with the polymer solution using a conventional automatic spray coating air system in a conventional coating pan at a temperature of 30° C. The spray operation was continued until the addition of an average of 10 mg. (dry weight basis) of polymeric material has been added to each tablet, after which the finished tablets were dried.

EXAMPLE 4

Following the procedure of Example 2, the polymeric coated tablets of Example 1 were tested for the dissolution rate of potassium chloride. The results are shown in Table IV. Each dissolution test represents an average of three tables.

The polymeric coating on each tablet remained intact throughout each test. The results show that the polymeric tablet coatings of this invention also give a satisfactory release rate of potassium chloride over the test period, without a release of solid potassium chloride from the tablet.

TABLE IV

| Time (hour) | Δ% Potassium Chloride Released* | | | | | |
|---|---|---|---|---|---|---|
| | 1 | 2 | 3 | 4 | 5 | Mean |
| 1 | 57.8 | 61.3 | 52.2 | 54.0 | 54.5 | 55.8 |
| 2 | 31.0 | 29.1 | 34.5 | 36.0 | 32.4 | 32.5 |
| 3 | 10.2 | 3.3 | 8.6 | 9.4 | 7.8 | 7.8 |
| 4 | — | 1.6 | 5.0 | — | 6.2 | 4.3 |
| % total released | 99.0 | 95.3 | 100.3 | 99.4 | 100.9 | 98.9 |

*Δ% = % difference between 2 successive time intervals

EXAMPLE 5

Polymeric coated tablets were prepared having the following composition:

| Tablet Core Ingredients | Amount per Tablet |
|---|---|
| Phenylpropanolamine HCl, powder U.S.P. | 75 mg |
| Lactose, powder U.S.P. | 205 mg |
| Calcium Sulfate, Dihydrate, N.F. | 85 mg |
| Microcrystalline Cellulose[1] | 130 mg |
| Alginic acid[2] | 32 mg |
| Stearic Acid, U.S.P. | 14 mg |
| Colloidal Silicon Dioxide, N.F. | 5 mg |
| Polyvinylpyrrolidone[3] | 14 mg |
| Tablet Core Weight | 560 mg |

[1]Avicel, pH 101, FMC Corp., Philadelphia, PA
[2]Kelacid, Kelco, Clark, NJ
[3]Povidone U.S.P., GAF Corp., N.Y., NY Tablet cores were coated with 10 mg polymer coatings. The polymer coating had the following composition:

| Polymer Coating Ingredients | Amount per Tablet |
|---|---|
| Polymethyl Methacrylate[4] | 2.0 mg |
| Polyethyl Glycol 4000 | 4.3 mg |
| Polyvinylacetate[5] | 3.0 mg |
| Diethyl Phthalate | 0.7 mg |
| Coating Weight | 10 mg |
| Coated Tablet Weight | 570 mg |

[4]Plexiglas VS, Rohm and Haas, Spring House, PA
[5]AYAF Resin, Union Carbide Corp., New York, NY 113,000 average viscosity molecular weight.

A batch of 5,000 (2.8 kg.) polymer coated phenylpropanolamine HCl tablets were prepared as follows:

375 gms. of phenylpropanolamine HCl, 1025 gms. lactose, 425 gms. of calcium sulfate, dihydrate, 650 gms. of microcrystalline cellulose, 160 gms. of alginic acid, 70 gms. of stearic acid, and 25 gms. of colloidal silicon dioxide, were screened through a #20 mesh stainless steel screen. The powders were then blended in a planetary mixer for 20 minutes. The blended powders were then granulated with a solution of 70 gms. of polyvinylpyrrolidone in 580 ml. of purified water. The granulation was then dried in an oven at 5020 C., and sized through a #18 mesh screen and compressed into 560 mg. tablets.

Tablet Specifications

Tablet Weight: 560 mg.
Tablet Thickness: 5.85–6.05 mm
Tablet Shape: 11 mm, round, deep convexity
Tablet Hardness: 10–12 Strong-Cobb Units A 2.5 kg. batch of the tablets were coated with the polymer coating.

The polymer solution used for coating was prepared by adding with constant stirring, 29.2 g. of polymethyl methacrylate, 62.8 g. of polyethylene glycol 4000, and 43.8 g. polyvinylacetate, to a solution of 518 gms. of methanol, absolute and 1336 gms. of methylene chloride. 10.2 gms of diethyl phthalate was then added.

The 2.5 kg. tablet batch was coated with the polymer solution using a conventional automatic spray coating air system in a conventional coating pan. The spray operation was continued until the desired addition of polymeric material has been added to each tablet, after which the finished tablets were dried.

EXAMPLE 6

The procedure and apparatus used for determining the dissolution rate of the phenylpropanolamine HCl tablets of Example 3 is that basically disclosed by C. Cakiryildiz et al. Dissolution Studies with a Multichannel Continuous-Flow Apparatus, J. Pharm. Sci., Vol. 64, No. 10, October 1975, p. 1692–1696, without the automatic sampling-recording unit.

The apparatus consisted of:

(a) dissolution cells immersed in a constant temperature bath maintained at 37°±0.5° C. (b) one reservoir vessel connected to each dissolution cell.

The reservoirs contained 500 ml. of distilled water as the medium, stirred at high speed and immersed in a constant temperature bath of 37°±0.5° C.

(c) a peristaltic pump connected to each dissolution cell and its reservoir vessel.

Standard Solution (0.15 mg/ml)

30.0 mg. of phenylpropanolamine in 200 ml. volumetric flask diluted to volume with 0.1N HCl.

The procedure consisted of:

(a) Every hour up to 8 hours, withdraw 10.0 ml. out of the dissolution vessel, and transfer to a 125 ml. separatory funnel, and replace the volume with 0.1N HCl.

(b) To each aliquot withdrawn, and to a 10.0 ml. portion of the standard solution, add 1.6 ml. of 1N NAOH and 1.5 ml. of 0.3N sodium metaperiodate (6.4 gm. in 100 ml. of distilled water). Mix and let stand 10 to 30 minutes.

(c) Extract with 3×20 ml. of chloroform filtering the extracts through chloroform washed cotton into a 100 ml. volumetric flask. Wash the cotton with a small amount of chloroform and adjust to volume with chloroform.

(d) Determine the absorbance of the standard and sample solutions with a suitable spectrophotometer in a 1 cm. cell between 330 mm. and 240 mm. using chloroform as a blank.

Calculation $$M_n = A_n \times f + \left[ c \times f \sum_{i=1}^{n-1} A_n \right]^* = A_n \times \frac{0.15}{A_{Std}} \times 500 + \left[ 0.02 \times \frac{75}{A_{Std}} \times \sum_{i=1}^{n-1} A_n \right]^*$$

% released: $\frac{M_n \times 100}{75}$  Δ% released: $\frac{(M_n - M_{n-1}) \times 100}{75}$ where $M_n$ = mg. released.

$A_n$ = absorbance of sample $n$.

$f = \frac{C_{Std}}{A_{Std}} \times$ dilution factor $c$ = correction factor = $\frac{\text{volume withdrawn}}{\text{total volume}}$ Δ% = % difference between two successive withdrawals.

*Correction for the amount of phenylpropanolamine HCl removed from the medium during the previous withdrawals.

The results of the dissolution rate tests of the phenylpropanolamine HCl tablets of Example 3 is shown in Table V. Each dissolution test represents an average of three tablets.

The polymer coating on each tablet remained intact throughout each test. These results show that the polymeric tablet coatings of this invention also give a satisfactory release rate of phenylpropanolamine HCl over the test period, without a release of solid phenylpropanolamine HCl from the tablet.

TABLE V

| Time (Hour) | 10 mg Polymeric Coating % Phenylpropanolamine HCl Released | | | | |
|---|---|---|---|---|---|
| | 1 | 2 | 3 | 4 | mean |
| 1 | 78.5 | 52.3 | 46.2 | 29.2 | 51.6 |
| 2 | 101.5 | 98.5 | 90.8 | 73.8 | 91.2 |
| 2.5 | 105.4 | 101.5 | 94.6 | 88.5 | 97.5 |
| 4 | 105.4 | 105.3 | 96.2 | 93.8 | 100.2 |
| Total % released | 105.4 | 105.3 | 96.2 | 93.8 | 100.2 |

What is claimed is:

1. A method of protecting the gastric mucosa from the effects of gastric irritating drugs which comprises releasing a gastric irritating drug core formulation from a gastric mucosa protecting polymeric coating material comprising from about 10 to 30 parts of polymehtyl methacrylate, from about 20 to 55 parts of polyethylene glycol, from about 20 to 60 parts of polyvinylacetate, and from about 5 to 10 parts of diethylphthalate, wherein the gastrointestinal fluid permeates the coating, dissolves the gastric irritating drug allowing it to diffuse in solution in the gastrointestinal area.

2. A method of protecting the gastric mucosa from the effects of gastric irritating drugs which comprises releasing a gastric irritating drug core formulation from a gastric mucosa protecting material comprising from about 10 to 30 parts of polymethyl methacrylate, from about 20 to 55 parts of polyethylene glycol, from about 20 to parts of polyvinylacetate, from about 5 to 10 parts of diethylphthalate, and from about 0.2 to 1.0 parts of dioctyl sodium sulfosuccinate, wherein the gastrointestinal gluid permeates the coating, dissolves the gastric irritating drug allowing it to diffuse in solution into the gastrointestinal area.

* * * * *